(12) United States Patent
Haerst et al.

(10) Patent No.: US 11,498,271 B2
(45) Date of Patent: Nov. 15, 2022

(54) FLUID SUPPLY SYSTEM FOR A 3D PRINTER

(71) Applicant: Kumovis GmbH, Munich (DE)

(72) Inventors: Miriam Haerst, Garching (DE); Stefan Leonhardt, Garching (DE); Stefan Fischer, Garching (DE); Sebastian Pammer, Garching (DE)

(73) Assignee: Kumovis GmbH, Munich (DE)

( * ) Notice: Subject to any disclaimer, the term of this patent is extended or adjusted under 35 U.S.C. 154(b) by 0 days.

(21) Appl. No.: 16/753,253

(22) PCT Filed: Sep. 28, 2018

(86) PCT No.: PCT/EP2018/076466
§ 371 (c)(1),
(2) Date: Apr. 2, 2020

(87) PCT Pub. No.: WO2019/068581
PCT Pub. Date: Apr. 11, 2019

(65) Prior Publication Data
US 2020/0298480 A1    Sep. 24, 2020

(30) Foreign Application Priority Data

Oct. 2, 2017   (DE) ...................... 10 2017 122 849.7

(51) Int. Cl.
*B29C 64/209*   (2017.01)
*B33Y 30/00*   (2015.01)
(Continued)

(52) U.S. Cl.
CPC .......... *B29C 64/209* (2017.08); *B29C 64/118* (2017.08); *B29C 64/393* (2017.08); *B33Y 30/00* (2014.12)

(58) Field of Classification Search
CPC ..... B29C 64/25; B29C 64/255; B29C 64/364; B33Y 10/00
See application file for complete search history.

(56) References Cited

U.S. PATENT DOCUMENTS 6,033,301 A   3/2000 Suwa
6,722,872 B1  4/2004 Swanson et al.
(Continued)

FOREIGN PATENT DOCUMENTS

DE   102006014835 A1   10/2007
DE   102015111504 A1    1/2017
(Continued)

OTHER PUBLICATIONS

ISA European Patent Office, International Search Report Issued in Application No. PCT/EP2018/076466, WIPO, dated Dec. 12, 2018, 2 pages.

*Primary Examiner* — Joseph S Del Sole
*Assistant Examiner* — Mohamed K Ahmed Ali
(74) *Attorney, Agent, or Firm* — McCoy Russell LLP

(57) ABSTRACT

The present invention relates to a fluid supply system for a 3D printer including a fluid pressure generating device for generating a pressurized fluid flow and with a fluid heating device for heating the fluid flow, wherein the 3D printer has at least one construction chamber which is delimited by a construction chamber with respect to the surroundings of the 3D printer and is sealed in a fluid-tight manner, wherein the fluid pressure generating device, the fluid heating device and the construction chamber housing are in fluid connect ion, whereby the fluid flow can flow through the construction chamber, and wherein the fluid pressure generating device, the fluid heating device and the construction chamber hous- (Continued)

ing define a closed fluid circuit for the fluid flow which is heated by the fluid heating device before entry into the construction chamber.

19 Claims, 4 Drawing Sheets

(51) Int. Cl.
    *B29C 64/118*     (2017.01)
    *B29C 64/393*     (2017.01)

(56) References Cited

U.S. PATENT DOCUMENTS

| | | |
|---|---|---|
| 6,817,941 B1 | 11/2004 | Gatov |
| 2014/0301883 A1* | 10/2014 | Wiesner ............... B23K 26/142 419/1 |
| 2015/0110911 A1 | 4/2015 | Snyder |
| 2015/0174658 A1* | 6/2015 | Ljungblad ............... B22F 12/00 419/55 |
| 2017/0128601 A1 | 5/2017 | DeCiccio et al. |
| 2018/0304359 A1* | 10/2018 | Gibson ................... B22F 10/10 |

FOREIGN PATENT DOCUMENTS

| | | |
|---|---|---|
| EP | 2261009 A1 | 12/2010 |
| EP | 2492084 A1 | 8/2012 |
| EP | 3023228 A1 | 5/2016 |
| EP | 3173233 A1 | 5/2017 |
| WO | 2016063198 A1 | 4/2016 |
| WO | 2017040675 A1 | 3/2017 |
| WO | 2017108477 A1 | 6/2017 |

\* cited by examiner

FLUID SUPPLY SYSTEM FOR A 3D PRINTER

CROSS-REFERENCE TO RELATED APPLICATIONS

The present application is a U.S. National Phase of International Patent Application Serial No. PCT/EP2018/076466 entitled "FLUID SUPPLY SYSTEM FOR A 3D PRINTER," filed on Sep. 28, 2018. International Patent Application Serial No. PCT/EP2018/076466 claims priority to German Patent Application No. 10 2017 122 849.7 filed on Oct. 2, 2017. The entire contents of each of the above-referenced applications are hereby incorporated by reference for all purposes.

TECHNICAL FIELD

The present invention relates to a fluid supply system for at least one 3D printer with at least one fluid pressure generating device for generating a pressurized fluid flow and with at least one fluid heating device for heating the fluid flow.

BACKGROUND AND SUMMARY

In connection with the 3D print of plastics, especially for medical applications (e.g. for implants), the currently achievable component quality is in the focus of many scientific investigations. Two of the most important challenges that play a decisive role with regard to component quality are the component tolerance and the component sterility or particle precipitation.

DE 10 2015 111 504 A1, for example, already knows a 3D printing device, in particular an FFF printing device, with at least one print head unit, wherein the print head unit is intended in at least one operating state to melt a printing material formed at least partially by a high-performance plastic material, in particular a high-performance thermoplastic material.

Further, EP 2 261 009 A1 discloses an apparatus and a method for producing a three-dimensional object, wherein the apparatus comprises a vacuum pump coupled to a feed reservoir in order to generate an air flow through the feed reservoir.

In addition, EP 3 023 228 A1 shows an additive manufacturing device having a gas flow system to provide a gas flow over the area of the construction platform of the additive manufacturing device.

Furthermore, EP 3 173 233 A1 discloses a three-dimensional manufacturing device, which has a processing space that is heated by a processing space heating unit provided for this purpose.

In addition, U.S. Pat. No. 6,033,301 A discloses a combined fan-filter unit which is provided for filtering the air of an air circuit in a clean room.

Furthermore, U.S. Pat. No. 6,722,872 B1 shows a three-dimensional modeling device which is intended to build up three-dimensional objects inside a heated construction chamber.

In addition, U.S. Pat. No. 6,817,941 B1 shows a diffuser for generating a uniform air flow within a process chamber used e.g. in the production of semiconductor chips.

Moreover, US 2015/110911 A1 shows an environment monitoring and control unit, which is used for additive manufacturing technologies, for example, as an interface to their respective environments.

Furthermore, WO 2016/063198 A1 shows a method and an apparatus for manufacturing three-dimensional objects by "Fused Deposition Modelling", wherein the manufacturing apparatus comprises radiation heating elements which are able to heat a surface of the object to be manufactured exposed to them.

In addition, a clean room technology for 3D printers and so-called bio-printers are known from WO 2017/040675 A1.

From WO 2017/108477 A1, a method of producing a three-dimensional object with a "Fused Deposition Modelling" printer can also be found.

Based on the solutions proposed in the state of the art, these additive manufacturing devices still have the problem of high component distortion and inadequate sterility and insufficient absence from germs and particles for medical applications. A minimal contamination of the component is to be aimed for and is not yet achieved at present.

It is therefore the task of the present invention to further develop a fluid supply system for a 3D printer of the aforementioned type in a beneficial manner, in particular with regard to improving the distortion and sterility of a component produced by means of the 3D printer and to improving the energy efficiency of the fluid supply system.

According to the invention, this task is solved by a fluid supply system for a 3D printer having the features of claim 1. According to this, provision is made that a fluid supply system for at least one 3D printer, in particular an FFF 3D printer, is provided with at least one fluid pressure generating device for generating a pressurized fluid flow and with at least one fluid heating device for heating the fluid flow, wherein the 3D printer has at least one construction chamber which is delimited by means of at least one construction chamber housing with respect to the surroundings of the 3D printer and is sealed in a fluid-tight manner, wherein the fluid pressure generating device, the fluid heating device and the construction chamber housing are in fluid connection, whereby the fluid flow can flow through the construction chamber, and wherein the fluid pressure generating device, the fluid heating device and the construction chamber housing define a closed fluid circuit for the fluid flow which is heated by means of the fluid heating device before entry into the construction chamber.

It is also possible to provide a valve or an inflow of advantageously filtered ambient air in order to temper the construction space. In principle, provision may be made that even air gaps or air inflows of external air can be present or tolerated. Complete fluid tightness is not necessary. Moreover, additionally supplied cold air can be admixed to the heated circuit in order to cool the construction space even after pressure build-up.

The invention is based on the fundamental idea that, due to the construction of a closed fluid circuit, the fluid which has already flowed through the construction chamber of the 3D printer and which has been heated before its entry is not released unused from the construction chamber into the environment of the 3D printer after its exit. Instead, the partially heated fluid that leaves the construction chamber can be returned to the construction chamber due to the closed fluid circuit. This type of fluid circuit is particularly advantageous because the fluid leaving the construction chamber still has a significantly higher temperature compared to its ambient temperature. As a result, the amount of energy to be provided for reheating the fluid can be significantly reduced. On the one hand, the energy required to heat the fluid can be significantly reduced. On the other hand, the fluid heating device can be dimensioned so as to be much more space-saving and compact compared to the state of the art, since it does not have to heat the fluid from the ambient temperature to the desired construction chamber temperature. The heating of the construction chamber is particularly optimal for low-distortion processing of semi-crystalline thermoplastics. The at least partial heating of the construction chamber by an upstream heated fluid flow allows to realize a particularly homogeneous temperature distribution within the construction chamber. This homogeneous temperature distribution has an additional positive effect on distortion reduction during the processing of thermoplastics. All in all, the fluid supply system can therefore be designed so as to be much more efficient and cost-effective. Furthermore, it is no longer necessary to filter the particles out of the ambient air, since the already filtered air flow is continually circulated and this air flow is filtered again. As a result, fewer particles in total need to be filtered out of the airflow, which is why the filters can also achieve a longer service life.

Furthermore, it may be provided that the fluid supply system in its operational state is designed in such a way that the fluid flow can flow through the construction chamber in the form of an essentially laminar flow. The laminar flow through the construction chamber (with a laminar air flow, especially for creating clean room conditions) has the advantage, especially due to its directional flow characteristics (without cross flows), that the construction chamber is contaminated as little as possible with particles or germs contained in the fluid or carried along by the flow. Since the present invention is also used in the field of medical technology (e.g. for the manufacture of implants), the lowest possible contamination of the component to be manufactured has a particularly positive effect on its sterility. In this context, it is also conceivable that the fluid flow can flow through the construction chamber in the form of an essentially vertical laminar flow.

It is also conceivable that the 3D printer comprises at least one print head which is movable within the construction chamber in a multi-axial and/or multi-dimensional, in particular three-dimensional manner, and at least one construction platform, which are surrounded by the laminar flow of the fluid flow. The three-dimensionally movable print head and the laminar flow of the fluid flow around the print head and the construction platform allow that the product to be manufactured can be printed in laminar air flow, which is advantageous for sterility and asepsis as well as freedom from particles. The laminar flow around these components reduces in particular their contamination or deposits due to particles or germs present in the air. Since these two assemblies are in direct contact with the component to be manufactured, their sterile, particle-free and dirt-free surfaces are essential.

It is also conceivable that the fluid supply system comprises at least one construction chamber entrance area which is arranged upstream of the construction chamber housing and in which at least one flow alignment unit is arranged. The flow alignment unit serves advantageously to calm the fluid flow before entering the construction chamber. Since the fluid flow upstream of the flow alignment unit is swirled by the fluid pressure generating device, the fluid heating device as well as by piping and elbows, it is essential to align the fluid flow before entering the construction chamber. It is especially advantageous to design the construction chamber entrance area in the form of a diffuser. One possible geometric design of the diffuser can be a thin-walled hollow cone whose flow-related cross-sectional area enlarges linearly upstream towards the construction chamber.

Furthermore, it is possible that the flow alignment unit comprises a flow guiding structure, in particular a flow guiding body, for an at least partially laminar alignment of the fluid flow. Such a flow guiding structure is a component which is integrated into the overall device and enables a targeted and particularly efficient laminar alignment of the fluid flow and can thus be advantageously arranged within the construction chamber entrance area. The flow guiding structure allows to direct the fluid flow in such a way that the desired laminar flow can be achieved in the construction chamber entrance area. The flow guiding body may include a diffuser, for example. It is conceivable here, for example, that the diffuser is designed as a thin-walled hollow cone, the lateral surface of which is shaped in such a way that the hollow cone widens in the direction towards the construction chamber.

Furthermore, the flow alignment unit may be designed in such a way that an air curtain forms around the component and thus the component is not directly exposed to the flow. This makes it possible to reduce the component distortion. This is made possible in particular by the fact that no direct air flow hits the component, thus allowing the component to cool down evenly.

In addition, the fluid supply system may comprise at least one fluid sterilization and/or filtering device which is in fluid connection with the fluid pressure generating device, the fluid heating device and the construction chamber housing. Due to the fluid sterilization and/or filtering device, the fluid supplied to the construction chamber can be filtered and/or cleaned in a particularly efficient manner. The fluid sterilization and/or filtering device is located upstream (in relation to the direction of flow through the construction chamber). By suitably designing this device, the fluid before entering the construction chamber can be cleaned, sterilized and filtered in such a way that the construction chamber complies with the regulations and standards of EN ISO 14644 for clean rooms. The closed fluid circuit is particularly advantageous in this context. This is because the continuous circulation of the fluid within the fluid supply system involves that the already cleaned or filtered fluid is returned to the fluid sterilization and/or filtering device as from the first circulation. As a result, the filtering and/or sterilization of the fluid can be carried out with each circulation of the fluid, which has a decisive effect on the sterility and particle contamination of the component to be produced.

It is also conceivable that the fluid flow has a temperature in a range in particular from about 20° C. to about 400° C., preferably from about 30° C. to about 350° C. and particularly preferably from about 50° C. to about 300° C. The temperature ranges described above, in particular the temperature range from about 50° C. to about 300° C., are particularly advantageous for the production of thermoplastics using the 3D printer with as little distortion as possible. For example, thermoplastics can be selected from the group of high-performance thermoplastics. The high-performance thermoplastics can be polyether ketones (such as PAEK, PEKK, PEEK, PEEEK, PEEKK, PEKEKK), polyamides (such as PA 69, PA 612, PA 11, PA 12, PA 46, PA 1212, PA 6/12, PA 1010, PPA), polyphenylene sulfide PPS, polyamide imides, polysulfones (such as PAS, PSF, PES, PPSU, PSU, PESU) and/or polycarbonates PC and also thermoplastic polyimides (PEI, PAI, PESI). It is also conceivable that the thermoplastics are reinforced with fibers and/or particles.

Furthermore, it is conceivable that the fluid flow has a velocity, in particular a mean velocity, within the construction chamber in a range in particular from about 0.05 m/s to about 5 m/s, preferably from about 0.1 m/s to about 5 m/s and particularly preferably from about 0.2 m/s to about 3 m/s. The above-mentioned ranges of the mean velocity, in particular the velocity range from about 0.2 m/s to about 3 m/s, of the fluid flow can guarantee a reliable, in particular constant and homogeneous heating of the construction chamber of the 3D printer. This type of heating helps above all to significantly reduce component distortion when processing thermoplastics. Incidentally, a fluid flow through the construction chamber is required to meet the above-mentioned standard.

Furthermore, it is possible that the fluid sterilization and/or filtering device, the fluid pressure generating device, the fluid heating device and/or the construction chamber housing are temperature-resistant up to a maximum temperature of about 300° C. Up to a maximum temperature of about 300° C. of the fluid, essentially all relevant technical thermoplastics can be processed by the 3D printer. A maximum temperature of about 300° C. is therefore particularly efficient, advantageous and also necessary for the distortion-free processing of thermoplastics.

In addition, provision may be made that the fluid pressure generating device is a flow machine such as a turbo compressor, in particular a radial compressor, or a fan or centrifugal fan. Basically, a flow machine is a fan or a compressor, for example. This type of compressor generates a particularly low-pulsation or low-shock and thus constant pressurized fluid flow, so that pressure and temperature fluctuations within the construction chamber can also be minimized. As a result, an even more homogeneous temperature distribution within the construction chamber can be achieved. In particular, the radial compressor can also be designed as a radial fan that is temperature resistant up to about 300° C.

It is also conceivable that at least one pressure reducing device is arranged downstream of the turbo compressor. The pressure reducing device can be used in a particularly advantageous manner because it generates a certain back pressure for the turbo compressor, which makes the use of a centrifugal ventilator or blower with a temperature resistance of up to 300° C. compulsory for physical reasons. The pressure reducing device can be designed, for example, as a perforated plate or perforated diaphragm.

It is also conceivable that the pressure reducing device, the fluid sterilization and/or filtering device, the fluid heating device and/or the flow alignment unit are capable of generating at least a pressure reduction of the fluid flow of at least 50 Pa. This pressure reduction caused by the above-mentioned components has a particularly beneficial effect on the operation or the controllability and/or adjustability of the turbo compressor, in particular the temperature-resistant radial compressor. Furthermore, a radial compressor of dimensions suitable for the 3D printer can be operated particularly efficiently and advantageously in the presence of such a pressure loss.

Furthermore, it is possible that the fluid supply system comprises a particle measuring device which is provided for monitoring the operation of the 3D printer and arranged in the construction chamber entrance area between the flow alignment unit and at least one entry opening of the construction chamber housing. Such a particle measuring device is particularly important and advantageous for achieving a high component standard in terms of sterility and particle contamination, which is particularly required in medical technology. By using this particle measuring device, the monitoring of the entire fluid supply system of the 3D printer can also be optimized, since maintenance or replacement of the fluid sterilization and/or filtering device can be suggested based on the particle measurement, for example by a central electronic control and/or regulation unit of the 3D printer. Furthermore, based on the particle measurement, a 3D printing process can also be aborted if a certain limit value for particles within the fluid flow is exceeded. It is also conceivable that, based on the particle measurement, the fluid sterilization and/or filtering device can be bypassed by means of a bypass valve and a bypass line. In doing so, the bypass valve can open the bypass line until an adjustable limit value for particles within the fluid flow is exceeded. Especially when using very expensive fluid sterilization and/or filtering devices, the bypass line can result in a noticeable increase in their service life and extended maintenance intervals.

Furthermore, provision may be made that the fluid flow contains a fluid which is a gas, in particular air. The use of a gas, especially air, is particularly advantageous because of the almost unlimited availability of air and the resulting very simple handling.

It is also conceivable that the fluid supply system has at least one gas connection by means of which the fluid supply system can be filled with at least one process gas other than air, with the 3D printer not being in operation during filling. In this context, it is conceivable that the process gas is an inert gas. Specifically, the use of an inert gas prevents oxidation when the 3D printer processes thermoplastics that are susceptible to oxidation, which can further improve the component quality.

BRIEF DESCRIPTION OF THE FIGURES

Further details and advantages of the invention are now to be explained in more detail by means of an exemplary embodiment shown in the drawings in which.

DETAILED DESCRIPTION

Figure 1:
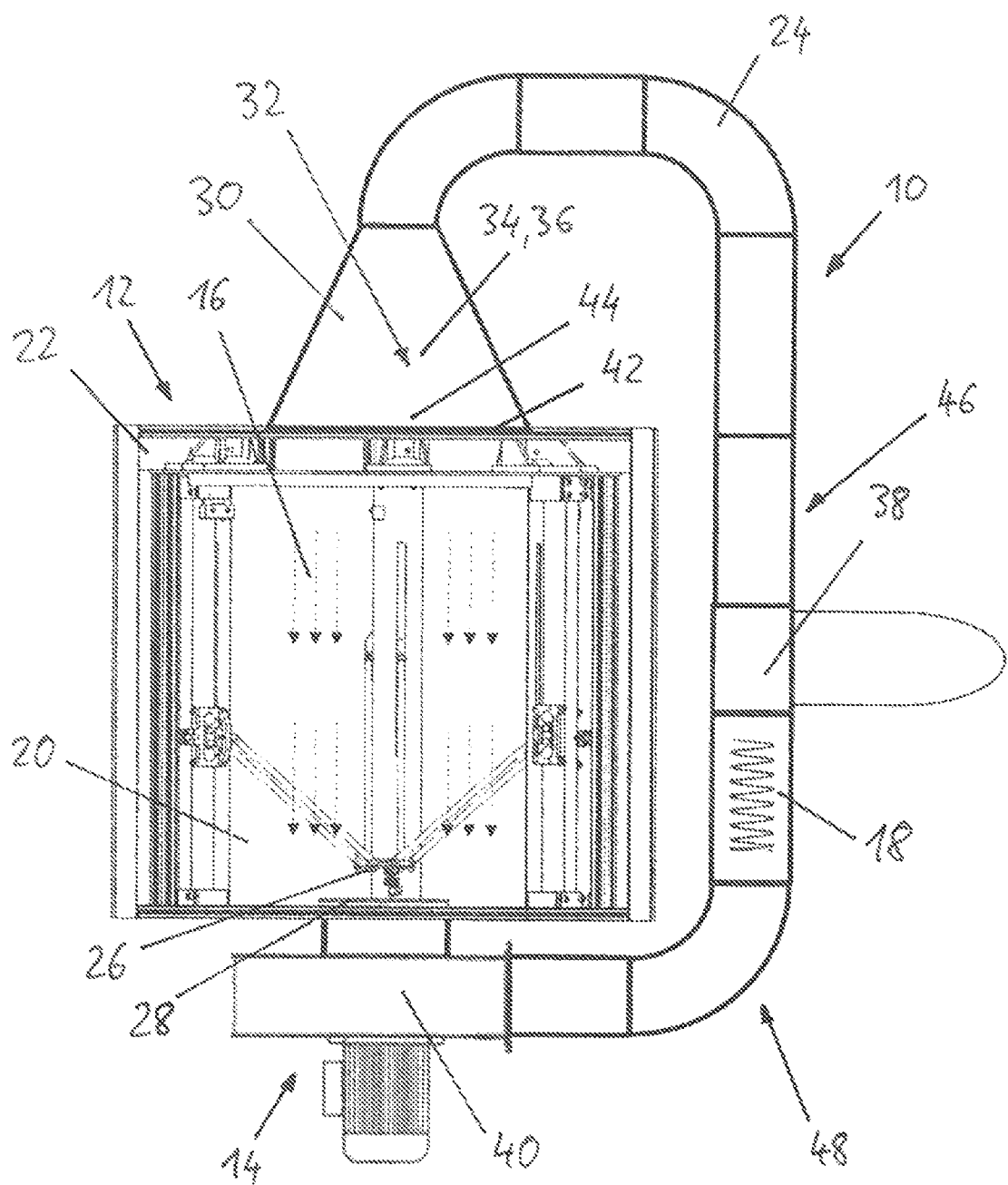
FIG. 1 is a schematic representation of an exemplary embodiment of a fluid supply system according to the invention for a 3D printer.

FIG. 1 shows a schematic representation of an exemplary embodiment of a fluid supply system 10 according to the invention for a 3D printer 12.

By way of example, a 3D printer 12 comprising a Delta kinematic system or also a Cartesian system can be used as 3D printer 12. In principle, the 3D printer 12 can also be a multidimensional printer and/or a printer with a multi-axis printing system.

The 3D printer 12 is designed as an FFF 3D printer (FFF: Fused Filament Fabrication).

The fluid supply system 10 includes a fluid pressure generating device 14 for generating a pressurized fluid flow 16.

The fluid flow 16 contains a fluid which is a gas.

The gas can be either air or a process gas such as an inert gas.

Furthermore, the fluid supply system 10 comprises a fluid heating device 18 for heating the fluid flow 16.

The 3D printer 12 also has a construction chamber 20 which is limited and sealed from the environment of the 3D printer 12 in a fluid-tight manner by a construction chamber housing 22.

In addition, the fluid pressure generating device 14, the fluid heating device 18 and the construction chamber housing 22 are in fluid communication.

Thus, the fluid flow 16 can flow through the construction chamber 20.

Inside the construction chamber 20, the fluid flow 16 has a mean velocity in a range from about 0.2 m/s to about 3 m/s.

The fluid flow 16 can also have a mean velocity inside the construction chamber 20 in a range from about 0.05 m/s to about 5 m/s.

In addition, it is conceivable that the fluid flow 16 can have a mean velocity inside the construction chamber 20 in a range from about 0.1 m/s to about 5 m/s.

Moreover, the fluid pressure generating device 14, the fluid heating device 18 and the construction chamber housing 22 form a closed fluid circuit 24 for the fluid flow 16.

In particular, the fluid flow 16 has a temperature in a range from about 50° C. to about 300° C.

However, it is also conceivable that the fluid flow 16 can have a temperature in a range from about 20° C. to about 400° C.

It is also conceivable that the fluid flow 16 can have a temperature in a range from about 30° C. to about 350° C.

The fluid flow 16 has these temperature ranges especially inside the construction chamber 20.

The fluid flow 16 is also heated by the fluid heating device 18 before entering the construction chamber 20.

The 3D printer 12 also features a print head 26, which can be moved in multiple axes within the construction chamber 20, and a construction platform 28.

The print head 26 and the construction platform 28 are surrounded by the laminar flow of the fluid flow 16 when the 3D printer 12 is ready for operation.

The fluid supply system 10 also has a construction chamber entrance area 30.

The construction chamber entrance area 30 is located upstream of the construction chamber housing 22.

A flow alignment unit 32 is located inside the construction chamber entrance area 30.

The flow alignment unit 32 includes a flow guiding structure 34.

The flow guiding structure is designed as flow guiding body 36.

The fluid supply system 10 according to FIG. 1 also comprises a fluid sterilization and filtering device 38.

The fluid sterilization and filtering device 38 is in fluid connection with the fluid pressure generating device 14, the fluid heating device 18 and the construction chamber housing 22.

In addition, the fluid pressure generating device 14 is a radial compressor 40.

A pressure reducing device 42 is located downstream of the radial compressor 40 (in relation to the direction of fluid flow through the device).

The fluid supply system 10 also has a particle measuring device 44 for monitoring the operation of the 3D printer 12.

The particle measuring device 44 is located in the construction chamber entrance area 30 between the flow alignment unit 32 and an entry opening of the construction chamber housing 22.

In addition, the fluid supply system 10 has a gas connection 46.

The fluid supply system 10 shown in FIG. 1 also includes a pipe system 48 which forms the closed fluid circuit 24.

The pipe system 48 consists of several straight pipe sections and 90° elbows through which the radial compressor 40, the fluid heating device 18, the fluid sterilization and filtering device 38, the construction chamber entrance area 30 and the construction chamber 20 are in fluid communication with each other.

The radial compressor 40 is flanged to the construction chamber housing 22 at a construction chamber outlet, whereas the construction chamber entrance area 30 is flanged to the construction chamber housing 22 at a construction chamber inlet.

Between the radial compressor 40 and the construction chamber entrance area 30, the fluid heating device 18 and the fluid sterilization and filtering device 38 are arranged in the pipe system 48.

The fluid heating device 18 is located downstream of the radial compressor 40.

The fluid sterilization and filtering device 38 is located downstream of the fluid heating device 18 in the pipe system 48.

The fluid heating device 18 is designed as a flow heater which has an electrical heating element that may be in the form of a heating coil, for example.

The fluid sterilization and filtering device 38 may have an EPA, HEPA or ULPA filtering unit, for example.

The fluid sterilization and filtering device 38 may also have a separation efficiency according to the filter classes E10, E11, E12, H13, H14, U15, U16 or U17.

The functioning of the fluid supply system 10 can now be described as follows:

Before starting up the 3D printer 12, the fluid supply system 10 should first check whether the gas suitable for the printing process and the printing material is contained in the construction chamber 20.

This check can be done, for example, with a gas sensor which is positioned inside the pipe system 48 or in the construction chamber 20 and is able to determine the appropriate gas.

The determination of different gases may also require the use of several gas sensors.

The filling of the fluid supply system 10 with air as process gas (after the previously used gas has been evacuated) can be done for example via a supply and discharge valve located inside the pipe system 48.

The radial compressor 40 can be used to support or accelerate the filling process with air.

The 3D printer 12 is not in operation during filling.

After filling of the fluid supply system 10, the fluid supply system 10 is hermetically sealed from the ambient atmosphere by closing the supply and discharge valve (not shown in FIG. 1).

Even before the 3D-printer 12 is in operation, the air inside the fluid supply system 10 can be circulated by means of the radial compressor 40, thus achieving a pre-cleaning of the air.

During this pre-cleaning process, the fluid heating device 18 can already be in operation, which additionally preheats the construction chamber 20.

As soon as the construction chamber 20 has a construction chamber temperature adapted to the material and the component to be produced, the 3D printer 12 starts operating.

During operation of the 3D printer 12, the air leaving the construction chamber 20 is sucked in by the radial compressor 40, is compressed and then fed to the fluid heating device 18.

There, the air is heated to an adjustable or controllable temperature value and, after flowing out of the fluid heating device 18, is fed to the fluid sterilization and filtering device 38 where it is cleaned and filtered; subsequently, it flows downstream into the construction chamber entrance area 30.

Specifically, the fluid sterilization and filtering device 38, the fluid pressure generating device 14 in the form of the radial compressor 40, the fluid heating device 18 and the construction chamber housing 22 are temperature-resistant up to a maximum temperature of about 300° C. However, normal applications may also require lower maximum temperatures in the range from 150-200° C.

During the flow through the construction chamber entrance area 30 whose housing is designed as a diffuser and in which the flow guiding body 36 is arranged, there will build up a laminar alignment of the fluid flow 16.

The flow guiding body 36 thus serves at least partially for the laminar alignment of the fluid flow 16.

However, also the diffuser serves for the laminar alignment of the fluid flow 16.

In the state ready for operation, the fluid supply system 10 is therefore designed such that the fluid flow 16 can flow through the construction chamber 20 in the form of a laminar flow.

Within the construction chamber entrance area 30, the particle measuring device 44 can also measure the particle number before the air enters the construction chamber 20 and make it available as a measured variable to an electronic control unit.

The control unit (not shown in FIG. 1) is used to control a drive system (e.g. an electric motor) of the radial compressor 40 and the fluid heating device 18.

The control unit can be integrated into the fluid supply system 10 or arranged on the construction chamber housing 22.

Moreover, the control unit is electrically connected to all sensors located in the fluid supply system 10 and the construction chamber housing 20.

The fluid supply system 10 and the 3D printer 12 can therefore have one or more pressure and temperature sensors.

Between the construction chamber entrance area 30 and the construction chamber housing 22, the pressure reducing device 42 (e.g. in the form of a perforated plate) can be arranged, which at least partially generates the back pressure necessary for the operation of the radial compressor 40.

The back pressure is necessary to prevent the radial compressor 40 from "running up" in unrestrained manner, i.e. to avoid an unrestrained increase in the speed of the radial compressor 40.

In addition to the pressure reducing device 42, other elements can be involved in the pressure reduction function, such as a guiding means (e.g. the flow guiding body 36) and the fluid sterilization and filtering device 38.

Having flowed through the pressure reducing device 42, the fluid or air flow 16 flows into the construction chamber 20.

The pressure reducing device 42, the fluid sterilization and filtering device 38, the fluid heating device 18 and the flow alignment unit 32 can thus generate a pressure reduction of the fluid flow of at least 50 Pa.

The already heated fluid or air flow 16 then flows through the construction chamber 20 in the form of a laminar flow, so that it contributes to the desired heating of the construction chamber 20 and to the production of a component with as little distortion as possible using the 3D printer 12.

In addition, the pressure generated by the fluid flow 16 inside the construction chamber 20 should always be higher than the pressure surrounding the construction chamber 20 in order to avoid additional particle load and germ contamination from the environment or atmosphere.

After flowing through the construction chamber 20, the air flows out of it and is sucked in again by the radial compressor 40, so that the process described above is repeated.

This process is repeated until the printing process is completed or, for example, a malfunction occurs (e.g. a particle concentration which is too high).

The previously described process can also be carried out as described above with any other process gas than air, so that air as a fluid is to be considered as an example only.

If the process described above is to be carried out with a process gas other than air (e.g. an inert gas), the air must be evacuated from the fluid supply system 10 and the construction chamber 20 of the 3D printer.

The fluid supply system 10 can then be filled with a process gas other than air using the gas connection 46.

Figure 2:
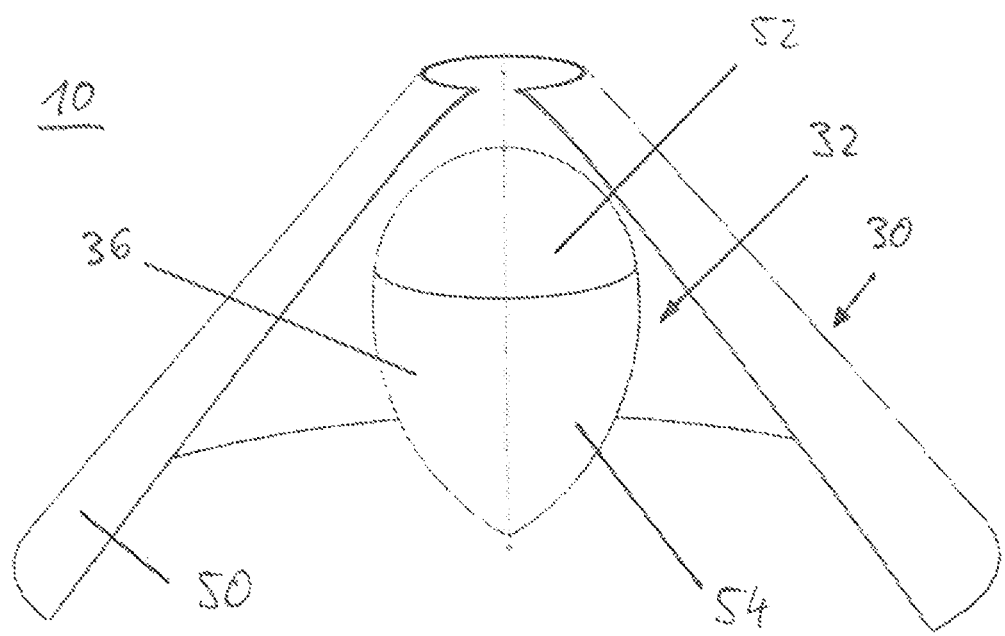
FIG. 2 is a partial sectional view of a construction chamber entrance area of the fluid supply system according to FIG. 1 and a flow guiding body arranged therein.

FIG. 2 shows a partial sectional view of the construction chamber entrance area 30 of the fluid supply system 10 according to FIG. 1 and a flow guiding body 36 arranged therein.

The construction chamber entrance area 30 consists of a diffuser 50 and the flow alignment unit 32 attached to the diffuser 50 and realized in the form of the flow guiding body 36.

The diffuser 50 is designed as a hollow cone whose shell surface is formed in such a way that it widens in a funnel shape toward the construction chamber (e.g. linear).

Two or more flow-optimized fastening struts (not shown in FIG. 2) can be provided to fasten the flow guiding body 36 to the inner wall of the diffuser 50.

The flow guiding body 36 according to FIG. 2 has a drop-shaped design with a half-dome 52 and a body of revolution 54 which is flush with the largest cross-sectional area of the half-dome and tapers towards the construction chamber.

The flow guiding body 54 tapers from the half-dome 52 along the longitudinal axis or rotational axis of the flow guiding body 36 and ends in a tip.

The flow guiding body 36 can be composed of the bodies described above or made in one piece.

The body of revolution 36 and the diffuser 50 are aligned so as to be coaxial.

The tip of the flow guiding body 36 faces the construction chamber 20.

Figure 3:
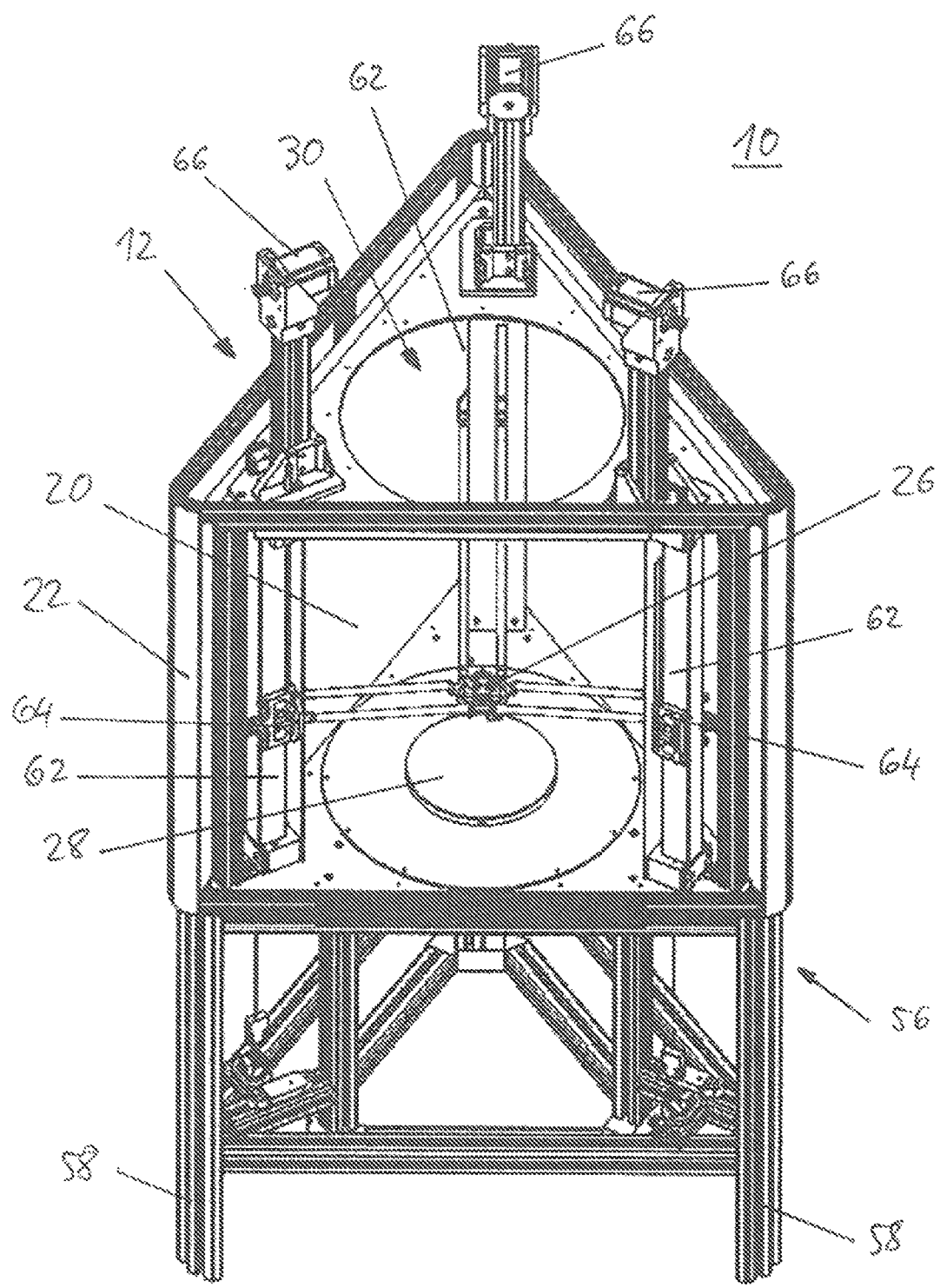
FIG. 3 is a schematic, perspective representation of a receiving frame for the 3D printer and for the fluid supply system according to FIG. 1.

FIG. 3 shows a schematic, perspective view of a receiving frame 56 for the 3D printer 12 and for the fluid supply system 10 according to FIG. 1.

The receiving frame 56 consists of three vertical profile supports 58, which are aligned to each other according to the corners of an equilateral triangle and are braced in a lattice-like manner by additional cross braces. In principle, however, it is not necessary for the ground plan to be triangular. Square, rectangular or other basic shapes or floor plans are also conceivable.

Attached to the receiving frame 56 is the construction chamber housing 22 which has an outer lattice-like frame 60 whose cross-section also has the shape of an equilateral triangle.

When mounted, the frame 60 has an upper and a lower panel, the lower panel being positioned below the upper panel in the direction of gravity so that the upper panel is spaced a certain height from the lower panel.

The upper and lower panels are also both formed as equilateral triangles, thus limiting the construction chamber 20 in addition to the outer frame 60.

The upper panel is also coupled to the construction chamber entrance area 30, whereas the lower panel supports the construction platform and is coupled to a housing of the radial compressor 40.

The three corner areas of the upper and lower panels are each connected by a vertically aligned linear guide 62 (i.e. a total of three linear guides 62), whose length corresponds to the height between the upper and lower panels.

The outer contour of each linear guide 62 also guides a carriage 64 which can slide vertically relative to it.

Each of the three carriages 64 has two ball-and-socket joints, to each of which a rod-shaped arm is hinged with its first end.

The second end of each arm is articulated to the print head 26, which also has two ball joints for each pair of arms for this purpose.

According to FIG. 3, the print head 26 thus has three pairs of ball joints in total, each of which being oriented towards one carriage 64 and to which two pairs of arms are linked in each case, starting from the three carriages 64.

When the print head 26 is assembled, both arms of each pair of arms are aligned to be parallel to each other.

The three-dimensional movement of the print head 26 within the construction chamber 20 thus follows from its kinematic linkage to the three carriages 64 by means of the arm pairs as well as from the respective vertical linear movements of the three carriages 64.

The vertical linear movement of each carriage 64 is achieved by an electric stepper motor 66 attached to the upper panel by means of a support so as to be located above said panel. Instead of an electric stepper motor 66, a servo motor or other drive unit can be used in principle.

Starting from the stepper motor 66, a belt (e.g. a toothed belt) extends along the entire length of the linear guide 62 which is of hollow design.

A magnetic coupling element (e.g. another internally guided carriage) is attached to the belt and transmits the linear movement of the belt by magnetic coupling to the externally guided carriage 64 arranged on the outer contour of the linear guide 62. Alternatively, the carriage can also be directly driven, e.g. by a cable pull system or a screw drive. In this way, the internal carriage and magnetic coupling can be dispensed with.

Figure 4:
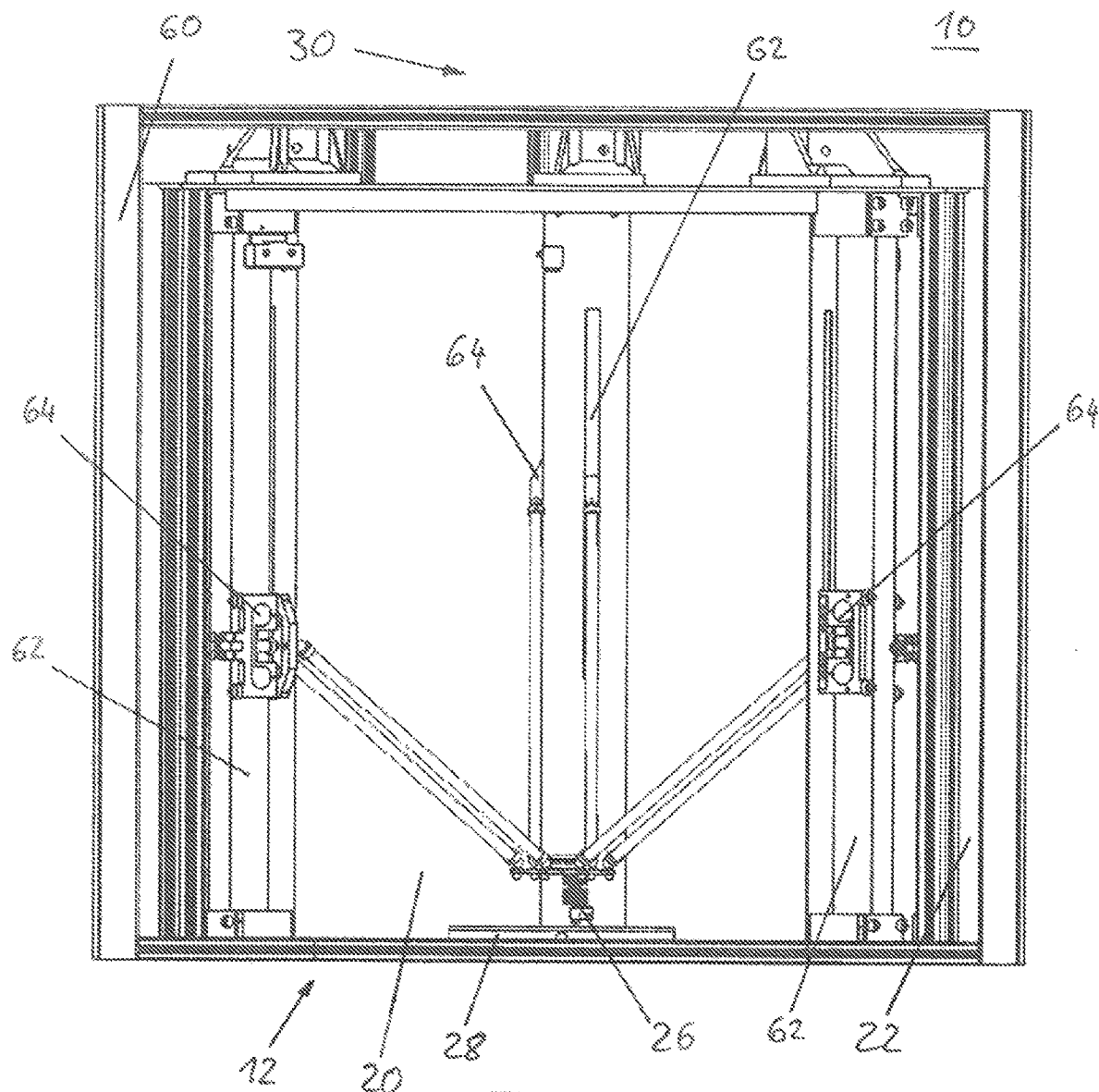
FIG. 4 is a schematic front view of the construction chamber of the 3D printer according to FIG. 1.

FIG. 4 shows an even more detailed schematic front view of the construction chamber 20 of the 3D printer 12 according to FIGS. 1 and 3.

LIST OF REFERENCE NUMERALS

10 fluid supply system
12 FFF 3D printer
14 fluid pressure generating device
16 fluid flow
18 fluid heating device, flow heater
20 construction chamber
22 construction chamber housing
24 fluid circuit
26 print head
28 construction platform
30 construction chamber entrance area
32 flow alignment unit
34 flow guiding structure
36 flow guiding body
38 fluid sterilization and filtering device
40 radial compressor
42 pressure reducing device
44 particle measuring device
46 gas connection
48 pipe system
50 diffuser
52 half-dome
54 body of revolution
56 receiving frame
58 profile supports
60 frame
62 linear guide
64 carriage
66 stepper motor

The invention claimed is:

1. A fluid supply system for a 3D printer comprising a fluid pressure generating device for generating a pressurized fluid flow and having a fluid heating device for heating the fluid flow, the 3D printer having a construction chamber which is delimited with respect to surroundings of the 3D printer by a construction chamber housing and is sealed in a fluid-tight manner, wherein the fluid pressure generating device, the fluid heating device, and the construction chamber housing are in fluid connection, where the fluid flow is configured to flow through the construction chamber, and wherein a closed fluid circuit for the fluid flow is formed by the fluid pressure generating device, the fluid heating device, and the construction chamber housing, which fluid flow is heated by the fluid heating device before entry into the construction chamber, wherein the fluid supply system comprises a construction chamber entrance area arranged upstream of the construction chamber housing and wherein the construction chamber entrance area comprises a diffuser which is attached to a flow alignment unit.

2. The fluid supply system according to claim 1, wherein the fluid supply system in an operational state is configured such that the fluid flow flows through the construction chamber in the form of a laminar flow.

3. The fluid supply system according to claim 2, wherein the 3D printer comprises at least one print head which is movable within the construction chamber in a multi-axial and/or multi-dimensional manner, and at least one construction platform, which are surrounded by the laminar flow of the fluid flow.

4. The fluid supply system according to claim 1, wherein the flow alignment unit comprises a flow guiding structure for an at least partially laminar alignment of the fluid flow.

5. The fluid supply system according to claim 1, wherein the fluid supply system comprises a fluid sterilization and/or fluid filtering device which is in fluid connection with the fluid pressure generating device, the fluid heating device, and the construction chamber housing.

6. The fluid supply system according to claim 1, wherein the fluid flow has a temperature in a range from about 20° C. to about 400° C.

7. The fluid supply system according to claim 1, wherein the fluid flow has a velocity within the construction chamber in a range from about 0.05 m/s to about 5 m/s.

8. The fluid supply system according to claim 5, wherein the fluid sterilization and/or fluid filtering device, the fluid pressure generating device, the fluid heating device, and/or the construction chamber housing are temperature-resistant up to a maximum temperature of about 300° C.

9. The fluid supply system according to claim 8, wherein the fluid pressure generating device is a flow machine.

10. The fluid supply system according to claim 9, wherein a pressure reducing device is arranged downstream of the flow machine.

11. The fluid supply system according to claim 10, wherein the pressure reducing device, the fluid sterilization and/or filtering device, the fluid heating device, and/or the flow alignment unit are capable of generating at least a pressure reduction of the fluid flow of at least 50 Pa.

12. The fluid supply system according to claim 11, wherein the fluid supply system comprises a particle measuring device which is provided for monitoring operation of the 3D printer and arranged in the construction chamber entrance area between the flow alignment unit and at least one entry opening of the construction chamber housing.

13. The fluid supply system according to claim 1, wherein the fluid flow contains a fluid which is a gas.

14. The fluid supply system according to claim 1, wherein the fluid supply system has at least one gas connection by which the fluid supply system is configured to be filled with at least one process gas other than air, with the 3D printer not being in operation during filling.

15. The fluid supply system according to claim 1, wherein the 3D printer is an FFF 3D printer.

16. The fluid supply system according to claim 3, wherein the at least one print head is movable within the construction chamber in a three-dimensional manner.

17. The fluid supply system according to claim 9, wherein the flow machine comprises a turbo compressor or a ventilator.

18. The fluid supply system according to claim 17, wherein the turbo compressor comprises a radial compressor.

19. The fluid supply system according to claim 13, wherein the gas comprises air.

* * * * *